United States Patent [19]

Helioff et al.

[11] Patent Number: 4,871,535
[45] Date of Patent: Oct. 3, 1989

[54] COMPOSITIONS USED IN PERMANENT STRUCTURE ALTERING OF HAIR

[75] Inventors: Michael W. Helioff, Westfield; Carmen D. Bires, Long Valley; Robert B. Login, Oakland, all of N.J.

[73] Assignee: GAF Corporation, Wayne, N.J.

[21] Appl. No.: 60,285

[22] Filed: Jun. 10, 1987

Related U.S. Application Data

[63] Continuation-in-part of Ser. No. 922,923, Oct. 24, 1986, Pat. No. 4,732,990.

[51] Int. Cl.$^4$ ................................................. A61K 7/09
[52] U.S. Cl. ..................................... 424/71; 132/204; 424/70; 424/78; 514/937
[58] Field of Search ............... 540/451, 531; 546/243; 548/550; 424/70, 71, 72, DIG. 3, DIG. 4, 62, 63, 64, 69, 71, 70, 78; 514/937

[56] References Cited

U.S. PATENT DOCUMENTS

| | | | |
|---|---|---|---|
| 4,035,478 | 7/1977 | Mullen | 424/70 |
| 4,272,511 | 6/1981 | Papantoniou et al. | 424/71 X |
| 4,348,380 | 9/1982 | Jacquet et al. | 424/70 X |
| 4,452,989 | 6/1984 | Deckner et al. | 424/69 X |
| 4,612,188 | 9/1986 | Zorayan et al. | 424/70 X |
| 4,676,263 | 6/1987 | Mahieu et al. | 424/72 X |
| 4,732,990 | 3/1988 | Login et al. | 546/243 X |

*Primary Examiner*—Joseph Paul Brust
*Attorney, Agent, or Firm*—Marilyn J. Maue; Joshua J. Ward

[57] ABSTRACT

A composition comprising an aqueous preparation on the basis of keratin softening, which contains as a hair swelling and penetration agent, a quaternized amino lactam having the formula:

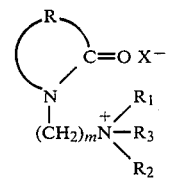

wherein m is an integer having a value of from 1 to 4; R is alkylene having from 3 to 8 carbon atoms and is optionally substituted with $C_1$ to $C_4$ alkyl; $R_1$, $R_2$ and $R_3$ are each independently selected from the group of alkyl, alkyleneoxy alkyl, alkylhydroxy, alkoxy, aryl, aralkyl, alkaryl, and alkylene amidoalkyl radicals, said groups each having from 1 to 30 carbon atoms and at least one of $R_1$, $R_2$ and $R_3$ is a radical having from 8 to 30 carbon atoms; and $X^-$ is a chloride, bromide or iodide anion. The invention also relates to the use of said quaternized compounds in hair structure altering compositions.

27 Claims, No Drawings

COMPOSITIONS USED IN PERMANENT STRUCTURE ALTERING OF HAIR

This application is a continuation-in-part of co-pending U.S. patent application Ser. No. 922,923, filed Oct. 24, 1986, entitled "QUATERNIZED NITROGEN CONTAINING COMPOUNDS" now U.S. Pat. No. 4,732,990.

In one aspect the invention relates to an aqueous composition containing a softening and penetrating agent for keratin protein reduction which agent enhances cleavage of the disulfide bond of the hair cysteine residue to form the corresponding cysteine residue in a process for altering the structure and/or configuration of hair as in straightening or permanent waving. In another aspect, the invention relates to an agent which promotes hard water solubility of a neutralizing lotion employed in a reducing process for altering the structure and/or configuration of hair.

BACKGROUND OF THE INVENTION

The activity or effectiveness of hair shaping preparations is based mainly on the inclusion therein of an agent for softening and relaxing the keratin protein present in hair by reducing the disulfide linkages of keratin. The hair fiber is wound on rods to achieve the desired waving effect or manipulated into a straightened condition and allowed to remain wetted with the reducing lotion for a desired period, after which the reducing lotion is rinsed off and finally oxidized with a neutralizing solution or air oxidized.

Basically, hair is softened and swelled by rupture of disulfide bonds present in the cysteine component of keratin by the use of a mild alkaline reducing agent. Cleavage of at least some of the disulfide bonding to form the corresponding cysteine residue is necessary to allow for molecular rearrangement which takes place during the hair fiber molding operation. The reductive fission of hair disulfides generally causes reddening of the scalp area and damage to the hair fiber, particularly hair which has been bleached, tinted or otherwise damaged. Current hair structure altering lotions which provide relaxation of imposed stress include aqueous solutions of alkaline mercapto compounds, sulfites or bisulfites at a pH of between 7 and 9.5. In order to obtain a permanent effect, particularly in hair straightening, it is often necessary to introduce the active agent in relatively high concentration with the result that the reducing lotion is provided at almost the limit of its physiological compatibility or tolerability.

Damage to hair is increased where heat waving, as opposed to cold waving, is employed. Of the reducing agents currently in use, the thioglycolates or thioglycolic acid, dithioglycolic acid and mercapto compounds such as ammonium thioglycolate, glyceryl, monothioglycolate, mercapto propionic acid and mercapto ethyl amine are most often employed in professional waving or hair straightening. Alkaline sulfites and bisulfites are generally reserved for home permanent use. In addition to the reducing agent, alkalis having a dissociation constant less than $5 \times 10^{-3}$, are also used to facilitate diffusion through the hair. These promotors include ammonia, ammonium hydroxide, ethanol amine, diisopropanol amine, glycine, and lysine.

In an attempt to minimize these harmful effects polymeric quaternized amines have been developed as reducing agent supports, e.g. see U.S. Pat. No. 4,579,732. These basic compounds have not been found to be completely satisfactory for the reason that they react with anionic components which are often present in hair structure altering compositions. Additionally the terminal amino groups react with hydrogen peroxide to form nitrogen oxides, thus increasing the effective amounts of peroxide which must be employed in fixing solutions. Since peroxides are known to have a hair drying effect, it is desirable to maintain the peroxide at a minimum level. In addition the large molecular size of these polymeric products prevents their penetration into the hair fiber and instead forms a coating over the hair which is subject to tack under conditions of high humidity. Further, many reducing lotions produce a disagreeable odor during reduction of the cysteine molecule which the polymeric amines are unable to overcome. Finally, the relatively high viscosity of these quaternized polymers together with the normal variations in molecular weight in the polymer chains in the product lead to formulation problems in reproducibility of product quality and in storage of the product over extended periods.

All of the commercial reducing lotions cause some degree of hair damage depending on the tightness and thickness of the curl, the temperature of processing, the concentration of the alkaline reducing agent and the condition of the hair. Accordingly, the art continues to seek means and possibilities whereby to provide for the aforesaid waving and straightening lotions, compositions which are less damaging to the skin and hair and which contain stable components simple to incorporate into the standard reducing lotions currently in use so as to provide the same or more effective results for heat or cold permanent waving and hair straightening. One method for the realization of these objects can be achieved by promoting penetration of the reducing lotion and providing absorption at a faster rate so that the time hair fiber is exposed to chemical action is reduced.

Secondary aims for permanent waving compositions include masking the thiol odor of the reducing lotion, providing non-degradable compounds which may be easily and reproduceably formulated and minimizing skin irritation caused by routine exposure of professional hair dressers or erythema on the scalp and neck of the subject undergoing treatment.

Accordingly, it is an object of this invention to achieve the various aims enumerated above by a simple and commercially feasible process involving the addition of the compound of the present invention as a component in standard hair structure and configuration altering lotions used both professionally and at home.

Another object of the invention is to provide an additive to hair reducing lotions which promotes a higher degree of curl in a shorter period of time.

Another object of the invention is to provide an additive which actually conditions the hair undergoing restructuring treatment.

Another object is to provide a compound which, when added to a hair waving or straightening lotion, increases the penetration rate of the lotion to minimize run-off and dripping.

Yet another object is to provide a long lasting hair permanent that moisturizes and protects the hair fiber so as to give the processed hair a silky softness.

Still another object is to provide an additive which improves hard water solubility of components in the neutralizing lotion.

Still another object is to provide a non-polymeric compound of reproduceable composition which is substantially non-reactive with respect to anionic components and hydrogen peroxide.

These and other objects of the invention will become apparent from the following description and disclosure.

THE INVENTION

In accordance with the present invention there is provided a quaternized amino lactam which is incorporated into a hair waving or straightening lotion at a concentration of between about 0.01 to about 7 wt. %, preferably between about 0.05 and about 5 wt. % based on total weight of the respective treating lotions. The amino mono-lactams of the present invention are defined by the structure

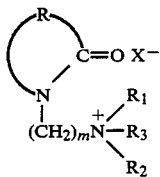

wherein m is an integer having a value of from 1 to 4; R is alkylene having from 3 to 8 carbon atoms and is optionally substituted with $C_1$ to $C_4$ alkyl; $R_1$, $R_2$ and $R_3$ are each independently selected from the group of alkyl, alkyleneoxy alkyl alkylhydroxy, alkoxy, aryl, aralkyl, alkaryl, and alkeyleneamidoalkye, radicals, said groups each having from 1 to 30 carbon atoms and at least one of $R_1$, $R_2$ and $R_3$ is a radical having from 8 to 30 carbon atoms; and $X^-$ is a chloride, bromide or iodide anion, preferably a chloride ion. Of these, the lactams having the formula

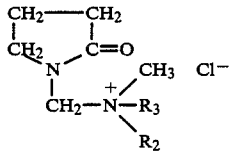

are preferred and include those pyrrolidones wherein at least one of $R_2$ and $R_3$ is octadecyl, hexadecyl, tetradecyl, hydrogenated tallow or coco and wherein the other of $R_2$ and $R_3$ is methyl or the same is $R_3$; and of these, most preferred are the pyrrolidones wherein $R_3$ is hexadecyl or octadecyl, which are employed in a reducing lotion at a concentration of between about 0.75 and about 1.50 wt. %.

As the term "lotion" is used herein, it will be understood to include a cream, a gel, an emulsion or a watery liquid.

The present lactams can be used individually or in admixtures and can be used to replace any of the promoters commonly present in commercial hair waving or straightening lotions including heat or cold permanent waving preparations utilizing water wrap or lotion wrap procedures. Alternatively, structural hair altering preparations may be made up using the components normally included in preparations currently marketed and the quaternized amino lactam added to enhance properties. In general, hair waving preparations comprise a reducing lotion and an oxidizing lotion; although some preparations are formulated such that the oxidizing or neutralizing lotion can be omitted. Most home perm and milder waving lotions can simply be washed off the hair fiber by rinsing with water and are therefore categorized as self-neutralizing.

Generally, the hair waving or straightening lotion contains a mild reducing agent which is exemplified by the most commonly used ammonium thioglycolate in a solution having a pH of between about 7 and 10.5, preferably between about 8.5 and about 9.5. Other reducing agents which have found commercial use include glyceryl monothioglycolate employed at a pH of less than 7, thioglycolic acid, dithioglycolic acid, mercaptoethyl amine, mercaptopropionic acid, dithioglycolate and alkali sulfites or bisulfites. The sulfite and bisulfite reducing agents are more commonly employed for home permanents and produce a milder, softer wave. The rate of reaction of these reducing agents increases with pH and temperature, although most are applied at between room temperature and 35° C. for a period of from about 3 to about 20 minutes. The concentration of reducing agent in the aqueous reducing lotion can vary between about 1 and about 20%. Within this range, lower concentrations are employed for damaged or bleached hair whereas for virgin, undamaged hair a concentration in the upper portion of the range can be applied. In the present invention the mole ratio of reducing agent to quaternized amino lactam is between about 3:1 and about 30:1, preferably between about 8:1 and about 20:1.

The reducing lotion is generally employed with an alkali having a dissociation constant less than $5 \times 10^{-3}$. Suitable compounds for alkalization include ammonia, ammonium hydroxide, sodium hydroxide, ethanol amine, diisopropanol amine, an alkali metal salt of an amino acid, e.g. glycine or lysine and guanidine. Alkali in a concentration of between about 0.5 and about 6% or 0.7–1.3 grams of free ammonia per 100 milliliters of solution is normally used.

The reducing lotion may also include a buffer such as ammonium bicarbonate to maintain a desired pH. Other additives which may be employed include catalysts for self-neutralizing permanent wave lotions, opacifiers to promote creamy appearance and fragrance to mask the odor of ammonia and thiol. Fatty acid polypeptide condensates, oxyethylated fatty alcohols and oxyethylated alkyl phenols have been employed as conditioners and emollients to minimize hair damage. However, these conditioning agents only minimally protect against hair damage and do not provide a sufficient moisture barrier to eliminate dryness and splitting at the distal ends of the hair fiber when processed with the reducing lotion. Similarly, the quaternized polymeric amines of large molecular dimensions merely coat the hair fiber and do not penetrate as do the present lactams of much smaller molecular size. Also, the lactam moiety, particularly the pyrrolidonyl moiety, of the present compounds exerts a stabilizing effect on the quaternized amino group so that the present compounds so as to minimize reaction with peroxides or anionic components. This stabilizing effect enables the use of smaller amounts of these components to achieve the desired effect.

The reducing lotions of the present invention are generally employed as 50–98% aqueous solutions of deionized water, preferably between about 75 and about 95% aqueous solutions.

The hair can be prerinsed with water or the reducing solution applied directly on the hair wound rods or in a straightened condition for softening and relaxation of the hair fiber. The softening effect is produced by rupture of the disulfide bonds of the cysteine residue in the keratin protein to produce the corresponding cysteine residue which can be represented for example by the following reaction

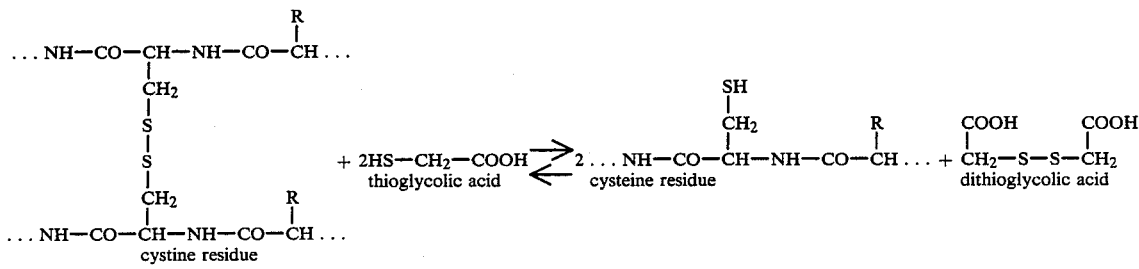

In this relaxed state, the hair fiber, wound on rods or straightened according to the desired structure, is held at room temperature, or slightly increased temperature up to about 50° C. for acceleration of the chemical reaction, for a period of between about 5 and about 20 minutes; after which the reducing solution is water washed from the hair and the disulfide bond are reformed by air oxidation or by the application of an oxidizing lotion which sets the hair according to the desired structure. The degree of curl depends primarily on the size and shape of the rods on which the hair is wound.

Reformation of the cysteine residue by oxidation is considerably high, for example up to 90% reformation. Thus, the oxidizing solution which neutralizes the reducer can be regarded as a fixing lotion. Suitable oxidizing agents include hydrogen peroxide, potassium bromate, sodium bromate, calcium bromide, sodium perborate, sodium persulfate, sodium iodate, potassium percarbonate and, for the removal of sulfite or bisulfite reducing agents, 8 to 12% of barium chloride or calcium chloride has been used effectively. Other oxidizing agents are employed in 1 to 20% solutions in water; although hydrogen peroxide is usually employed as a 1 to 2% aqueous solution.

Some typical reducing hair waving lotions are illustrated by the following formulations.

| SINGLE STEP WAVING FORMULATION | |
|---|---|
| Ingredients | % By Weight |
| Ammonium thioglycolate | 0.20 |
| Potassium sulfite | 0.80 |
| Tartaric acid | 0.03 |
| Ethyl alcohol | 1.00 |
| Monoethanolamine | 0.03 |
| Potassium iodide | 0.60 |
| Water | 97.34 |

| BISULFITE WAVING FORMULATION | |
|---|---|
| Ingredients | % By Weight |
| Water | 55.55 |
| Ammonium bisulfite | 22.00 |
| Hydroxyethyl cellulose | 2.50 |
| Urea | 10.00 |
| Isopropyl alcohol | 5.00 |
| Disodium phosphate | 1.14 |
| Citric acid | 0.46 |
| Ammonium hydroxide | 1.10 |
| Chelating agent | 0.05 |
| Fragrance | 0.20 |

| BISULFITE WAVING FORMULATION | |
|---|---|
| Ingredients | % By Weight |
| Surfactant | 2.00 | and

| Ingredients | % by Weight |
|---|---|
| Sodium bisulfite | 6.46 |
| Sodium borate | 4.10 |
| Sodium carbonate | 4.10 |
| Monoethanolamine | 4.92 |
| Diethanolamine | 4.92 |
| Wetting agent | 1.00 |
| Water | q.s to 100.00 |

The basic technical premise underlying permanent hair straightening is similar to that in waving. Hair is softened, maintained straight under tension for a period of time by means of the high viscosity of the product and repeated combing, and after rinsing, rehardened by application of the neutralizer. Many hair-straightening compositions are merely thickened versions of permanent-waving products. For example, alkaline thioglycolate (6-8%) is formulated into thick oil-water emulsion or cream using generous concentrations of cetyl and stearyl alcohols and high molecular weight polyethylene glycol together with a fatty alcohol sulfate as emulsifier which offers an added advantage of ready rinsability. Mixtures of ammonium bisulfite and urea have also found application in hair-straightening. Processing time may be between about 30 minutes and 2 hours, depending on the initial curliness of the hair. Conventional oxidizing neutralizers e.g. $H_2O_2$, bromates, and perborates are most often used in the final step of the process. The reformation of the cysteine cross-linkages in bisulfite-reduced hair is effected by a rinse (pH 8-10).

An important class of permanent straighteners in frequent use is based on alkali as an active ingredient. Sodium or potassium hydroxide or sodium carbonate in combination with guanidine are used at concentrations of 1.5-3% in a heavy cream base. Although the recommended treatment time is only 5-20 minutes for this mixture, the straightening effects, in general, surpass those obtained with either thioglycolates or bisulfites because of the greater aggressiveness of the alkaline relaxers. It has been found that a 15-minute treatment irreversibly decreases the cysteine content of hair to about two thirds of its initial value.

The damaging action of strong alkali on hair is not restricted to the disulfide bonds alone. Apart from the potential of the main-chain scission, the very nature of the high pH base leads to a build-up of negative charges in hair which results in increased swelling, the latter being intensified by concurrent breakdown of the disulfide bonds.

Typical formulations for hair straightening preparations include the following Examples A–D

| | Ingredients | % By Weight |
|---|---|---|
| A | Petrolatum | 76.75 |
| | Polyoxyethylene oleyl ether | 21.00 |
| | Lactic acid, 90% | 2.20 |
| | Thymolphthalein | 0.05 |
| B | Water | 42.25 |
| | Sodium hydroxide | 2.20 |
| | Sodium lauryl ether sulfate | 6.00 |
| | Hydrolyzed animal protein | 1.00 |
| | Mineral oil | 21.30 |
| | Petrolatum | 8.00 |
| | Squalene | 3.00 |
| | Lauryl alcohol | 1.25 |
| | Lanolin fatty acids | 2.00 |
| | Cetyl alcohol | 12.00 |
| | Sodium isostearoyl-2-lactylate | 1.00 |
| C | Emulsifying wax NF (Polawax) | 7.5 |
| | Cetyl alcohol (Crodacol C-95) | 1.0 |
| | Petrolatum (Protopet) | 4.0 |
| | Carnation mineral oil | 15.0 |
| | Steareth 2 (Volpo S-2) | 0.5 |
| | DEA-oleth-10 phosphate (Crodafos N10N) | 1.5 |
| | Propylene glycol | 2.0 |
| | Steareth 10 (Volpo S-10) | 2.5 |
| | Deionized water | 53.0 |
| | NaOH, 25% | 12.0 |
| | Diazolidinyl urea (and) methylparaben (and) propylparaben (and) propylene glycol (Germaben II) | 1.0 |
| D i | Carbomer 941 (Carbopol 941) | 2.0 |
| | Deionized water | 77.8 |
| | Triethanolamine | 1.0 |
| ii | Ammonium thioglycolate | 13.2 |
| | Ammonia | 3.5 |
| | Laureth-23 (Emthox 5964) | 0.5 |
| | Quaternium-33 (and) ethyl hexanediol (Lanoquat 1756) | 2.0 |

Solutions (i) and (ii) are combined.

Typical oxidizing and neutralizing formulations for permanent waving or straightening lotions include the following.

| HEAT HAIR WAVE NEUTRALIZING SOLUTION | |
|---|---|
| | Wt. % |
| Hydrogen peroxide | 1.3000 |
| Citric acid | 0.5000 |
| Phosphoric acid, adjusted to pH 2.84 | 0.0064 |
| Water | q.s to 100.0000 |

| NEUTRALIZER WITH CITRATE BUFFER | |
|---|---|
| | Wt. % |
| Hydrogen peroxide, 35% sol. | 5.00 |
| Isostearamidopropylmorpholine lactate | 0.75 |
| Cetearyl alcohol/ceteth 20 | 0.50 |
| Mineral oil | 0.07 |
| Methylparaben | 0.10 |
| Phenacetin | 0.10 |
| Fragrance | 0.05 |
| Citric acid | 4.00 |
| Water | q.s. to 100.00 |
| Sodium citrate | q.s. to pH 1.9 |

| COLD WAVE NEUTRALIZER WITH KERATIN HYDROLYZATE | |
|---|---|
| | Wt. % |
| Sodium bromate | 5.0 |
| Amphoteric surfactant | 0.5 |
| Cationic cellulosic | 0.5 |
| Perfume | 0.1 |
| Keratin hydrolyzate | 2.0 |
| Water | q.s. to 100.0 |

The present lactams, preferably the pyrrolidones, of the present invention can be applied to either or both the reducing and oxidizing lotions employed for permanent waving or straightening of hair to achieve remarkable benefits in the overall processing. Such benefits include a higher degree of curl and curl retention over an extended period, high lubricity on the hair, significant elimination of erythema, masking of thiol odor, hair conditioning action during processing, faster and higher penetration of reducing lotion into the hair and lotion viscosity increase. The present lactams do not react with hydrogen peroxide or other peroxygenated compounds; thus, the amount of oxidizing agent can be minimized to only that required to neutralize the reducing solution. The lactams of this invention are also non-reactive with anionics so that they may be incorporated into a wide variety of testing solutions.

Because of their excellent hair penetration and stability the present lactams can be used in much smaller amounts than required for prior promoters while accomplishing at least the same, more often better, and faster results. Incorporation of the present lactams results in hair having excellent wet and dry compatibility, improved body and hair of a smooth, soft, lustrous and silky texture after processing It is theorized that the quaternized amino lactam, particularly the quaternized amino pyrrolidone, penetrates deeply to the cortex of the hair fiber and protects the shaft against damage from within. The present N-alkyl lactams appear to provide a moisture barrier around the hair shaft and gives high substantivity to the hair without interfering with the relaxing process. Further, the present lactams can tolerate usage over a very wide pH range without precipitating out of solution. These and many other advantages are realized by the use of the present compounds.

The lactam compounds of this invention are prepared by the process described in detail in co-pending U.S. patent application, Ser. No. 922,923, filed Oct. 24, 1986, entitled "QUATERNIZED NITROGEN CONTAINING COMPOUNDS".

Having generally described the present invention, reference is now had to the following examples which illustrate preferred embodiments but which are not to be construed as limiting to the scope of the invention as more broadly set forth above and in the appended claims.

EXAMPLE 1

Design Freedom* permanent waving preparation was used as the standard professional hair waving preparation for this test. This professional product contained a waving lotion and a neutralizing lotion represented as follows.

* Zotos International Inc., Darien, Conn.

| REDUCING LOTION | % by Weight |
| --- | --- |
| Ammonium thioglycolate (60 wt. %) | 15.20 |
| Ammonium hydroxide (28 wt. %) | 0.80 |
| Ammonium Bicarbonate buffer | 0.80 |
| Styrene/PVP Copolymer latex Opacifier | 1.60 |
| Igepal CA 630 Surfactant** | 0.20 |
| Deionized water | 81.00 |
| Fragrance | 0.40 |

*Zotos International Inc., Darien, Connecticut
**1% Aqueous solution of $C_8H_4\text{-}C_6H_4\text{-}O\text{-}(CH_2CH_2O)_{av.9}CH_2CH_2OH$ $$CH_8H_4-C_6H_4-O-(CH_2CH_2O)_{av.9}CH_2CH_2OH$$

| NEUTRALIZING LOTION | % by Weight |
| --- | --- |
| Hydrogen peroxide | 4.50 |
| Citric acid | 0.20 |
| Polyoxyethylene lauryl ether | 0.50 |
| Latex opacifier | 0.10 |
| Phenacetin | 0.04 |
| Deionized water | 94.26 |
| Fragrance | 0.40 |

The subject on which this experiment was performed had hair of normal type, medium texture, good condition and of medium length. The hair of test subject was saturated with water, allowed to drip dry, after which the hair was sectioned into about 25 sections and the distal ends of each section is wrapped in a porous end paper and rolled on a permanent hair setting rod.

To a one half portion of the above reducing lotion, 1.00% by weight of dimethyl hexadecyl-[N-(2-pyrridonyl) methyl] ammonium chloride (QS-470) was added and thoroughly mixed. The resulting reducing lotion was then uniformly applied to the rolled sections of hair on a one half area (left side) of the scalp. To the remaining portion of reducing lotion 1% of Igepal CO-630* was added, mixed and uniformly applied to the remaining rolled sections of hair on the other half section (right side) of the scalp. The reducing lotions were allowed to remain on the hair for a period of 8 minutes at room temperature, after which the rolled hair was thoroughly rinsed with water, allowed to drip dry and a neutralizing lotion uniformly was then applied to saturate the hair. The neutralizing solution was allowed to remain on the hair for 3 minutes, after which the hair was rinsed and the rods removed. The hair was again rinsed and brush dried.

* ethoxylated nonylphenol,

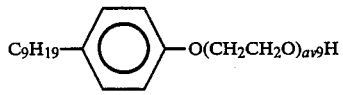

The left half section of the head treated with the reducing lotion containing the present lactam possessed excellent wet and dry compatibility, and the hair had a silky soft texture characteristic of conditioning. The remaining half section of the hair to which the reducing lotion containing no lactam was applied, showed noticeably less compatibility and softness and less curl.

The results of additional specific tests are reported in following Table I.

EXAMPLES 2-6

The general procedure outlined above in Example 1 was repeated on a different second subject whose hair condition was of normal type but long and coarse. In both of the following tests, 1% of lactam based on total composition, was added.

In one half of the reducing lotion, dimethyl hexadecyl-[N-(2-pyrrolidonyl)methyl] ammonium chloride (QS-470) was added and thoroughly mixed. The resulting lotion was uniformly applied to hair rolled sections on the left side of the scalp. To the remaining portion of the reducing lotion, dimethyl octadecyl-[N-(2-pyrrolidonyl)methyl] ammonium chloride (QS-570) was introduced and mixed to provide a uniform composition. This later composition was uniformly applied to the subject's scalp on the right side. The remaining procedure is as described in Example 1 and the results of this Example are also shown on Table I.

Table I reports the results of permanent waving test comparisons on the second subject.

TABLE I

| | First Subject | | Second Subject | |
| --- | --- | --- | --- | --- |
| Subject Tested | left side | right side | left side | right side |
| WAVE LOTION | | | | |
| masked thio odor | good | better | good | better |
| test curl (after 3 minutes) | excellent | excellent | good | excellent |
| scalp sensation | none | none | none | none |
| process time | 15 min. | 15 min. | 15 min. | 15 min. |
| penetration | excellent | good | good | excellent |
| NEUTRALIZATION | | | | |
| penetration | excellent | good | good | excellent |
| pick up | excellent | good | good | good |
| thio odor | good | better | good | better |
| scalp sensation | none | none | none | none |
| HAIR EVALUATION | | | | |
| frizz | none | none | none | none |
| snarling | none | none | little | none |
| breakage | none | none | none | none |
| curl | excellent | good | good | excellent |
| springiness | excellent | good | good | excellent |
| luster | good | good | good | excellent |
| feel (smoothness) | excellent | good | good | excellent |
| residue on hair | none | none | none | none |
| odor masked | fair | better | fair | better |
| scalp and skin irritation | none | none | none | none |
| RE-EVALUATION AFTER 3 WEEKS | | | | |
| HAIR CONDITION | | | | |
| feel | very soft | soft | smooth | smoother |
| snarling | none | none | slight | none |
| breakage | very little | little | none | none |
| curl retention | good | good | good | excellent |
| skin and scalp irritation | none | none | none | none |

EXAMPLE 7

The permanent waving formulation employed in Example 1 is used with 2.00% by weight of methyl dioctadecyl-[N-(2-azacycloheptane-2-one)methyl] ammonium chloride in place of dimethyl-hexadecyl-[N-(2-pyrrolidonyl) methyl] ammonium chloride in the reducing lotion.

When applied to the hair rolled on permanent hair setting rods, followed by application of the neutralizing solution employed in Example 1 and rinsed and dried in the manner described therein, the same hair conditioning benefits are achieved.

EXAMPLE 8

The permanent waving formulation employed in Example 1 is used with 1.5% by weight of dimethyl tetradecyl-[N-(2-piperidonyl)ethyl] ammonium chloride in the reducing lotion in place of dimethyl-hexadecyl-[N-(2-pyrrolidonyl)methyl] ammonium chloride in the reducing lotion.

When applied to the hair rolled on permanent hair setting rods, followed by application of the neutralizing solution employed in Example 1 and rinsed and dried in the manner described therein, the same hair conditioning benefits are achieved.

Comparable results are obtained when QS-470 or QS-570 are replaced with other quaternized amino lactams of this invention, particularly methyl-didodecyl-[N-(2-pyrrolidonyl)methyl]chloride methyl-dihexadecyl-[N-(2-pyrrolidonyl)methyl]chloride dimethyl-ecosyl-[N-(2-pyrrolidonyl)methyl]chloride methyl-dioctadecyl-[N-(2-pyrrolidonyl)methyl]-chloride.

Many other substitutions and modifications will become apparent from the foregoing disclosure without departing from the scope of this invention.

What is claimed is:

1. A permanent hair structure altering composition containing a permanent hair structure altering vehicle and an effective hair fiber penetrating amount of a quaternized amino lactam having the formula:

$$\begin{array}{c} R \\ \diagup \diagdown \\ \phantom{N} C=O \quad X^- \\ \diagdown \diagup \\ N \\ | \quad +\diagup R_1 \\ (CH_2)_m N - R_3 \\ \diagdown \\ R_2 \end{array}$$

wherein m is an integer having a value of from 1 to 4; R is alkylene linear having from 3 to 8 carbon atoms and is optionally substituted with $C_1$ to $C_4$ alkyl; $R_1$, $R_2$ and $R_3$ are each independently selected from the group of alkyl, alkyleneoxy alkyl alkylhydroxy, alkoxy, aryl, aralkyl, alkaryl, and alkylene amidoalkyl radicals, said groups each having from 1 to 30 carbon atoms and at least one of $R_1$, $R^2$ and $R_3$ is a radical having from 8 to 30 carbon atoms; and $X^-$ is a chloride, bromide or iodide anion.

2. A permanent structure altering composition for hair containing between about 0.01% and about 7.00% by weight, of the quaternized amino lactam of claim 1 wherein $R_1$ is methyl or alkyl containing from 14 to 22 carbon atoms.

3. The composition of claim 1 wherein said lactam is quaternized amino pyrrolidone.

4. The composition of claim 1 wherein said composition is a hair reducing lotion containing the quaternized amino lactam of claim 1.

5. The composition of claim 4 wherein the reducing lotion is an aqueous solution of ammonium thioglycolate and the quaternized amino lactam, is a quaternized amino pyrrolidone wherein $R^1$ is methyl or alkyl containing from 14 to 22 carbon atoms.

6. The composition of claim 4 wherein said reducing lotion is a permanent waving lotion.

7. The composition of claim 4 wherein said reducing lotion is a hair straightening lotion.

8. The reducing lotion of claim 4 containing between about 0.5% and about 5% by weight of said quaternized amino lactam.

9. The composition of claim 8 wherein said quaternized amino lactam is dimethyl hexadecyl-[N-(2-pyrrolidonyl)methyl]chloride and wherein the composition contains between about 0.75% and about 1.5% of said lactam in the hair reducing lotion.

10. The composition of claim 8 wherein said quaternized amino lactam is dimethyl octadecyl-[N-(2-pyrrolidonyl)methyl]chloride and wherein the composition contains between about 0.75% and about 1.5% of said lactam in the hair reducing lotion.

11. The composition of claim 1 wherein said composition contains a hair reducing lotion and a neutralizing lotion for said reducing lotion and said quaternized amino lactam is added to at least one of the reducing and neutralizing lotions in a concentration of between about 0.01% and about 7% by weight based on the total volume of each lotion.

12. The permanent hair structure altering composition of claim 1 wherein said lactam has the formula $$\begin{array}{c} CH_2 \!-\!-\! CH_2 \\ | \qquad\quad | \\ CH_2 \qquad C=O \\ \diagdown N \diagup \quad CH_3 \quad Cl^- \\ | \qquad +\diagup \\ CH_2 - N - R_3 \\ \diagdown \\ R_2 \end{array}$$

wherein at least one of $R_2$ and $R_3$ is selected from the group consisting of octadecyl, tetradecyl, hexadecyl, hydrogenated tallow and coco and the other of $R_2$ and $R_3$ is methyl or the same as $R_3$.

13. The process of contacting hair with a reducing lotion containing a keratin reducing agent and the quaternized amino lactam of claim 1 in a mole ratio of between about 5:1 and about 30:1.

14. The process of claim 13 wherein said reducing lotion is an aqueous solution containing between about 0.01 wt. % and about 7 wt. % of said reducing agent.

15. The process of claim 13 wherein the mole ratio of reducing agent to quaternized amino lactam is between about 8:1 and about 20:1.

16. The process of adding an effective hair penetrating amount of the quaternized amino lactam of claim 1 to a permanent hair reducing lotion.

17. The process of adding an effective hair penetrating amount of the quaternized amino lactam of claim 1 to a hair straightening lotion.

18. The process of claim 16 wherein said quaternized amino lactam is a quaternized amino pyrrolidone.

19. The process of claim 17 wherein said quaternized amino lactam is a quaternized amino pyrrolidone.

20. The process of claim 16 wherein said quaternized amino lactam is the quaternized amino lactam of claim 12.

21. The process of claim 17 wherein said quaternized amino lactam is the quaternized amino lactam of claim 12.

22. A process for permanently altering the configuration of hair without damage including the steps of
   (a) imparting the desired configuration to the hair
   (b) treating the hair with an aqueous alkaline solution containing a mercaptan keratin reducing agent and a quaternized amino lactam of claim 1 in a mole ratio of from about 3:1 to about 30:1 reducing agent to lactam at a pH of from about 7 to about 10.5 for a period sufficient to obtain a permanent hair configuration alteration without damage to the hair and (c) fixing said altered configuration with a neutralizing solution.

23. The process of claim 22 wherein the mole ratio of reducing agent to quaternized amino lactam is between about 8:1 and about 20:1.

24. The process of claim 22 wherein said neutralizing solution contains a peroxy oxidizing agent and the quaternized amino lactam of claim 1.

25. The process of claim 24 wherein said quaternized amino lactam is quaternized amino pyrrolidone wherein $R^1$ is alkyl having from 14 to 22 carbon atoms and between about 0.01% and about 7% of said lactam is contained in said neutralizing solution.

26. The process of claim 22 wherein said neutralizing solution contains a peroxy oxidizing agent and the quaternized amino lactam of claim 12.

27. The process of claim 22 wherein the quaternized amino lactam in the aqueous alkaline solution is the quaternized amino lactam of claim 12.

* * * * *